(12) United States Patent
DeRidder et al.

(10) Patent No.: US 7,901,458 B2
(45) Date of Patent: Mar. 8, 2011

(54) INTERVERTEBRAL SPACER AND INSERTION TOOL

(75) Inventors: Steven D. DeRidder, Barlett, TN (US); James D. Schwender, Edina, MN (US); Christopher I. Shaffrey, Charlottesville, VA (US); T. Andrew Simonton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 858 days.

(21) Appl. No.: 11/305,604

(22) Filed: Dec. 16, 2005

(65) Prior Publication Data

US 2007/0162128 A1  Jul. 12, 2007

(51) Int. Cl.
*A61F 2/44* (2006.01)

(52) U.S. Cl. ........ 623/17.11; 606/99; 606/246; 606/249; 623/17.16

(58) Field of Classification Search ............... 623/17.11, 623/17.12–17.16; 606/99, 86 A, 86 B, 914, 606/915, 916, 246, 249
See application file for complete search history.

(56) References Cited

U.S. PATENT DOCUMENTS

| | | | | |
|---|---|---|---|---|
| 1,489,458 A | * | 4/1924 | William | 81/380 |
| 4,616,534 A | * | 10/1986 | Park et al. | 81/99 |
| 4,878,915 A | | 11/1989 | Brantigan | |
| D330,835 S | * | 11/1992 | Culpepper | D8/23 |
| 5,306,309 A | | 4/1994 | Wagner et al. | |
| 5,425,772 A | | 6/1995 | Brantigan | |
| 5,609,636 A | | 3/1997 | Kohrs et al. | |
| 5,716,415 A | | 2/1998 | Steffee | |
| 5,728,159 A | | 3/1998 | Stroever et al. | |
| 5,865,845 A | | 2/1999 | Thalgott | |
| 5,888,226 A | | 3/1999 | Rogozinski | |
| 5,895,426 A | | 4/1999 | Scarborough et al. | |
| 5,899,939 A | | 5/1999 | Boyce et al. | |
| 6,025,538 A | | 2/2000 | Yaccarino | |
| 6,045,580 A | | 4/2000 | Scarborough et al. | |
| 6,066,174 A | | 5/2000 | Farris | |
| 6,123,731 A | | 9/2000 | Boyce et al. | |
| 6,131,491 A | * | 10/2000 | Hirse | 81/99 |
| 6,174,311 B1 | | 1/2001 | Branch et al. | |
| 6,200,347 B1 | | 3/2001 | Anderson et al. | |
| 6,224,607 B1 | * | 5/2001 | Michelson | 606/96 |

(Continued)

FOREIGN PATENT DOCUMENTS

WO    WO03026522 A    4/2003

(Continued)

OTHER PUBLICATIONS

European Patent Office, International Searching Authority,Notification of Transmittal of the International Search Report and the Written Opinion of the International Searching Authority or the Declaration, International Application No. PCT/US2006/061975, Aug. 20, 2007, 17 pages.

*Primary Examiner* — Eduardo C Robert
*Assistant Examiner* — Jan Christopher Merene

(57) ABSTRACT

An implant for placing in the spine is disclosed. The implant has a tool engaging surface on its trailing end configured for intimate engagement with an insertion tool. The insertion tool configuration is particularly suited for implants made of brittle materials including bone and bone substitutes. Also disclosed is an insertion tool having a gripping end adapted for intimate engagement with an implant. In one embodiment, the insertion tool is operable by axial movement of one gripping arm with respect to the other.

11 Claims, 11 Drawing Sheets

U.S. PATENT DOCUMENTS

| | | |
|---|---|---|
| 6,245,108 B1 | 6/2001 | Biscup |
| 6,258,125 B1 | 7/2001 | Paul et al. |
| 6,277,149 B1 | 8/2001 | Boyle et al. |
| 6,315,795 B1 | 11/2001 | Scarborough et al. |
| 6,342,074 B1 | 1/2002 | Simpson |
| 6,425,920 B1 | 7/2002 | Hamada |
| 6,440,444 B2 | 8/2002 | Boyce et al. |
| 6,443,987 B1 | 9/2002 | Bryan |
| 6,458,158 B1 | 10/2002 | Anderson et al. |
| 6,482,233 B1 | 11/2002 | Aebi et al. |
| 6,503,279 B1 | 1/2003 | Webb et al. |
| 6,511,509 B1 | 1/2003 | Ford et al. |
| 6,517,564 B1 * | 2/2003 | Grafton et al. ............... 606/213 |
| 6,520,993 B2 | 2/2003 | James et al. |
| 6,530,955 B2 | 3/2003 | Boyle et al. |
| 6,554,863 B2 | 4/2003 | Paul et al. |
| 6,558,424 B2 | 5/2003 | Thalgott |
| 6,562,072 B1 | 5/2003 | Fuss et al. |
| 6,579,318 B2 | 6/2003 | Varga et al. |
| 6,613,090 B2 | 9/2003 | Fuss et al. |
| 6,632,247 B2 | 10/2003 | Boyer et al. |
| 6,635,086 B2 | 10/2003 | Lin |
| 6,638,310 B2 | 10/2003 | Lin et al. |
| 6,648,915 B2 | 11/2003 | Sazy |
| 6,652,593 B2 | 11/2003 | Boyer et al. |
| 6,676,703 B2 | 1/2004 | Biscup |
| 6,696,073 B2 | 2/2004 | Boyce et al. |
| 6,706,067 B2 | 3/2004 | Shimp et al. |
| 6,719,794 B2 | 4/2004 | Gerber et al. |
| 6,761,739 B2 | 7/2004 | Shepard |
| RE38,614 E | 10/2004 | Paul et al. |
| 6,843,804 B2 | 1/2005 | Bryan |
| 6,843,805 B2 | 1/2005 | Webb et al. |
| 6,852,127 B2 | 2/2005 | Varga et al. |
| 6,855,167 B2 | 2/2005 | Shimp et al. |
| 6,902,578 B1 | 6/2005 | Anderson et al. |
| 6,964,687 B1 * | 11/2005 | Bernard et al. ............ 623/17.16 |
| 7,060,073 B2 * | 6/2006 | Frey et al. ........................ 606/85 |
| 7,235,082 B2 * | 6/2007 | Bartish et al. .................... 606/99 |
| 7,776,049 B1 * | 8/2010 | Curran et al. ..................... 606/99 |
| 2002/0165612 A1 * | 11/2002 | Gerber et al. .............. 623/17.11 |
| 2003/0009222 A1 * | 1/2003 | Fruh et al. .................. 623/17.11 |
| 2003/0028249 A1 * | 2/2003 | Baccelli et al. ............. 623/17.11 |
| 2003/0083747 A1 * | 5/2003 | Winterbottom et al. ... 623/17.11 |
| 2003/0105528 A1 * | 6/2003 | Shimp et al. ............... 623/17.16 |
| 2003/0135275 A1 | 7/2003 | Garcia et al. |
| 2003/0149438 A1 * | 8/2003 | Nichols et al. .................... 606/99 |
| 2004/0117020 A1 | 6/2004 | Frey et al. |
| 2005/0065613 A1 | 3/2005 | Gross et al. |
| 2005/0240267 A1 * | 10/2005 | Randall et al. ............. 623/17.11 |
| 2006/0235426 A1 * | 10/2006 | Lim et al. ......................... 606/99 |
| 2008/0097454 A1 * | 4/2008 | DeRidder et al. ................ 606/99 |
| 2008/0275455 A1 * | 11/2008 | Berry et al. ....................... 606/99 |

FOREIGN PATENT DOCUMENTS

WO     WO03037228 A     5/2003

\* cited by examiner

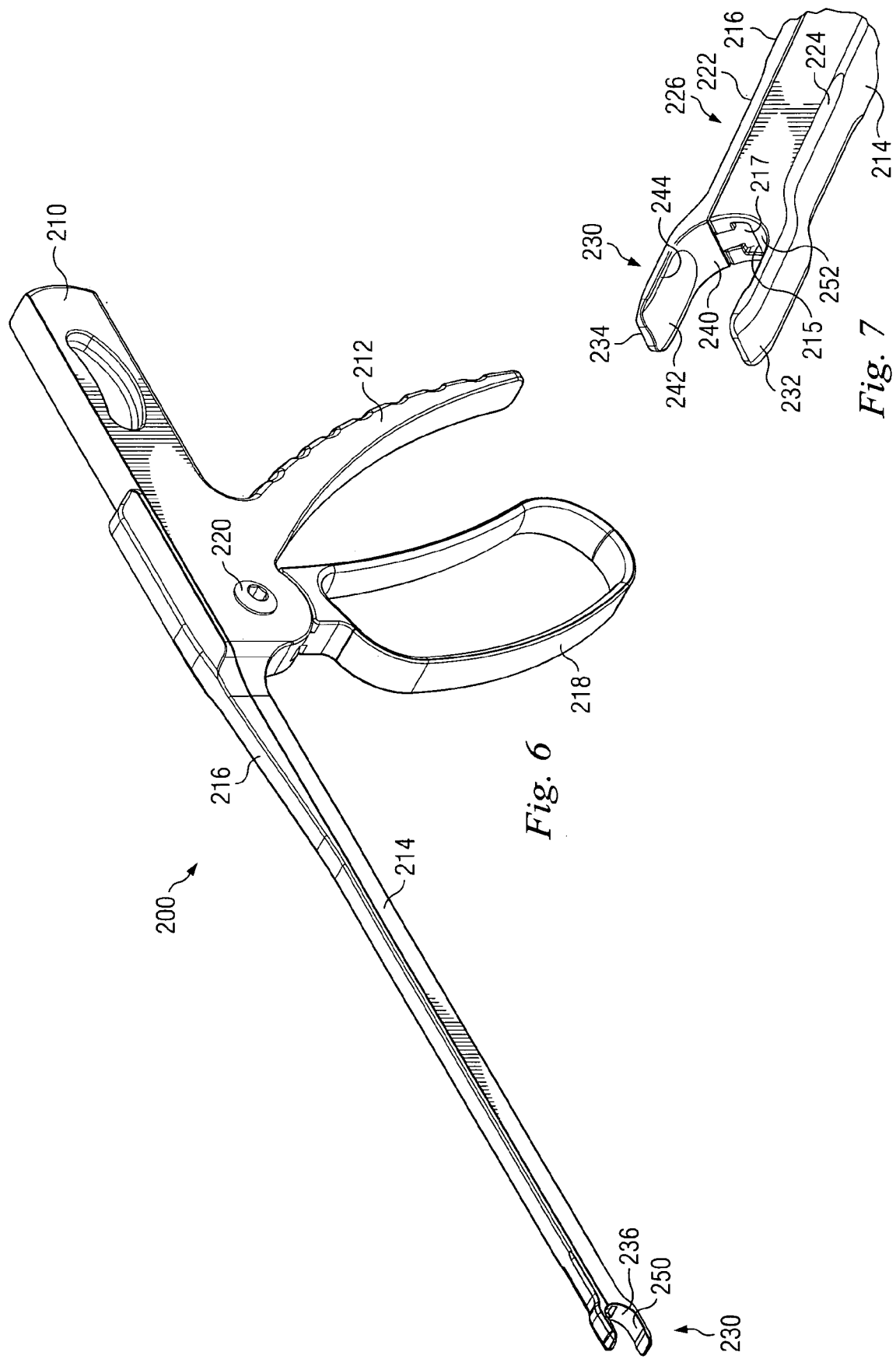

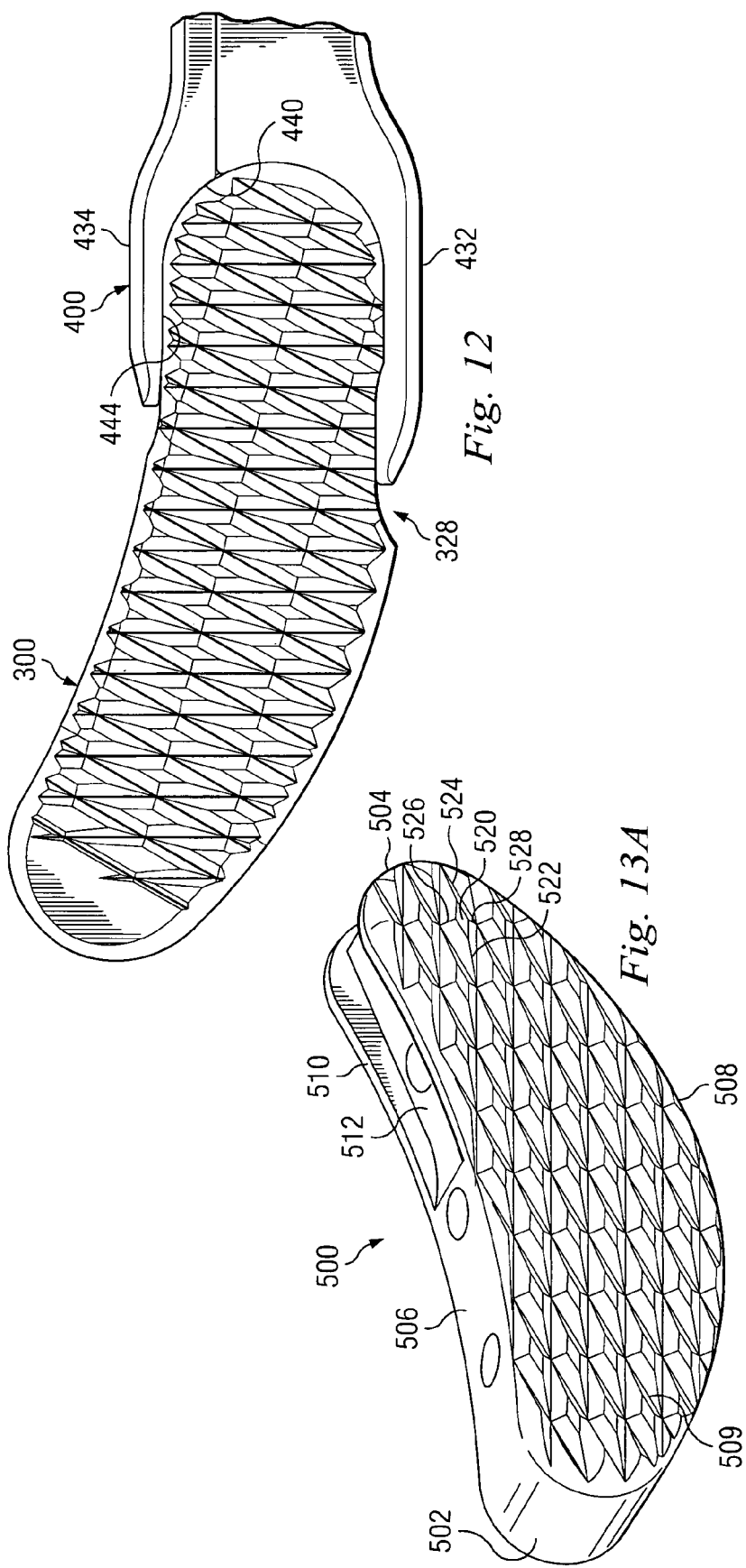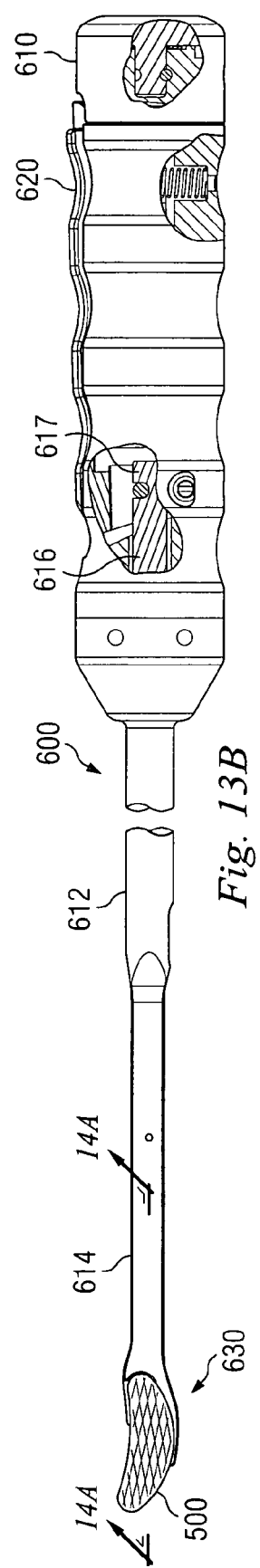

INTERVERTEBRAL SPACER AND INSERTION TOOL

FIELD OF THE INVENTION

The present invention is directed to improved implants, implant inserters and methods of their use. More particularly, the present invention is directed to spinal implants and instrumentation for use in performing interbody spine stabilizations.

BACKGROUND OF THE INVENTION

The present invention relates to interbody stabilization procedures of vertebrae in the spine, including fusions and disc space height restorations. A number of medical conditions such as compression of spinal cord nerve roots, degenerative disc disease, herniated nucleus pulposis, spinal stenosis and spondylolisthesis can cause severe low back pain. Restoration of the space between adjacent vertebrae and/or removal of the anatomical structure pushing against the spinal cord or exiting nerve roots is known to alleviate patient suffering. It is often desirable to stabilize the restored disc space by placing a spacer within the intervertebral space. Some intervertebral implants rest on the existing endplates while others either partially or completely extend into the adjacent intervertebral bodies. Access to the affected disc space is achieved from a variety of approaches to the spine which are the result of surgeon preference, patient anatomy, level of the spine affected and interbody implant selection.

A number of implant materials have been utilized to form interbody spacers. Many of these spacers are manufactured from metal or other very durable materials suitable for human implantation. Additionally, spacers are fashioned from bone, polymers, coral and other material suitable for implantation in the spine but having a greater tendency to fracture under high stresses.

In certain procedures, the loads applied to the implant during the insertion procedure exceed the loads that the implant may experience after implantation in the patient. The interface between the implant and the implant insertion tool may concentrate forces on weak areas of the implant during insertion. This area of concern is increased when implants are formed of materials having a tendency to crumble, crack or break as a result of experiencing high forces during insertion. For example, interbody fusion implants inserted from a transforaminal approach to the lumbar spine (TLIF approach) are typically forced to make a turn in the disc space to achieve the desired alignment. U.S. patent application Ser. No. 10/721,642 filed Nov. 25, 2003 by Frey et al. discloses instruments and techniques for unilateral implant positioning from a posterior approach to the spine and is incorporated herein by reference in it's entirety. It will be appreciated that in one aspect, the unilateral insertion technique uses the insertion tool to apply non-longitudinal forces to the implant to urge it across the disc space. Such forces may damage existing implants or inhibit the use of certain desirable materials for such implant designs.

Therefore, there remains a need for improved implant designs, configurations of the tool engagement surface on the implant, as well as improvement for the insertion tools utilized to grasp the implant during the insertion procedure.

SUMMARY OF THE INVENTION

The present invention provides an implant for insertion at least partially into the disc space between a first vertebra and a second vertebra. The implant comprises an implant body having a first surface for engaging the first vertebra and a second surface for engaging the second vertebra, and an insertion tool engaging configuration formed on the implant body. In one aspect, the configuration includes a first engagement surface oriented along a first axis and an opposed second engagement surface oriented along a second, offset axis. In a further aspect, the tool engagement configuration includes a groove in the trailing end of the implant and an aperture to receive a projection from the insertion tool.

In another aspect, the present invention provides an implant insertion tool configured for grasping an interbody spinal implant for insertion between two adjacent vertebrae. The insertion tool comprises a shaft having a longitudinal axis extending along at least a portion of its length and an implant grasping end. In one aspect, the implant grasping end includes a first stationary portion joined to said shaft and a second movable portion coupled to said shaft. The second movable portion is movable axially with respect to the first stationary portion substantially along the longitudinal axis from an open position for releasing and receiving an implant to a closed position for gripping an implant. In a further aspect, the gripping end defines a static socket for receiving an implant and includes a projection movable into the socket to hold the implant.

Further aspects, forms, embodiments, objects, features, benefits, and advantages of the present invention shall become apparent from the detailed drawings and descriptions provided herein.

BRIEF DESCRIPTION OF THE DRAWINGS

FIG. 6 is a perspective view of an implant insertion tool according to one embodiment of the present invention.

FIG. 7 is an enlarged perspective view of a portion of the implant insertion tool of FIG. 6.

FIG. 12 is a bottom top view of the spacer of FIG. 11 in combination with an alternative insertion tool.

FIG. 13A is a perspective view of an alternative embodiment of an implant according to the present invention.

FIG. 13B is a bottom view of the implant of FIG. 13A in combination with a alternative embodiment of an insertion tool.

DESCRIPTION OF THE PREFERRED EMBODIMENTS

Figure 1:
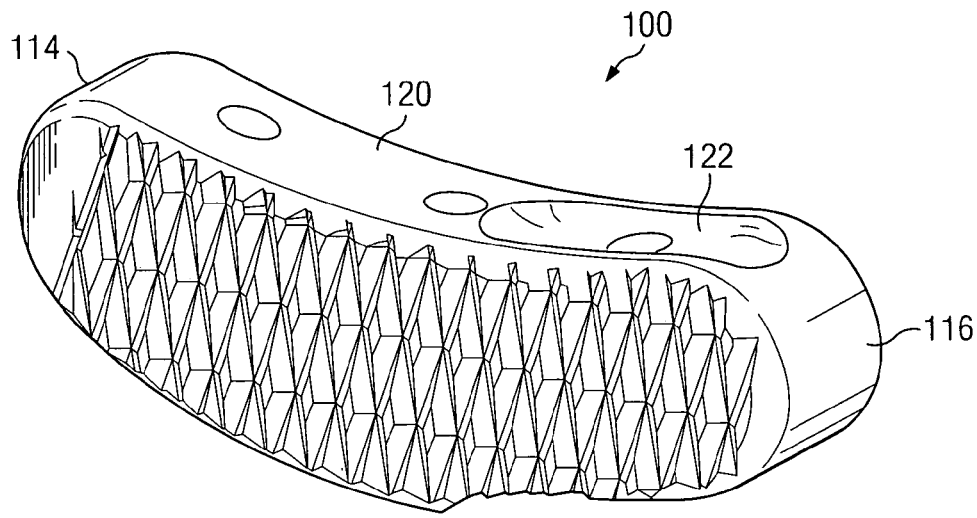
FIG. 1 is a perspective view of an implant according to one embodiment of the present invention.
Figure 2:
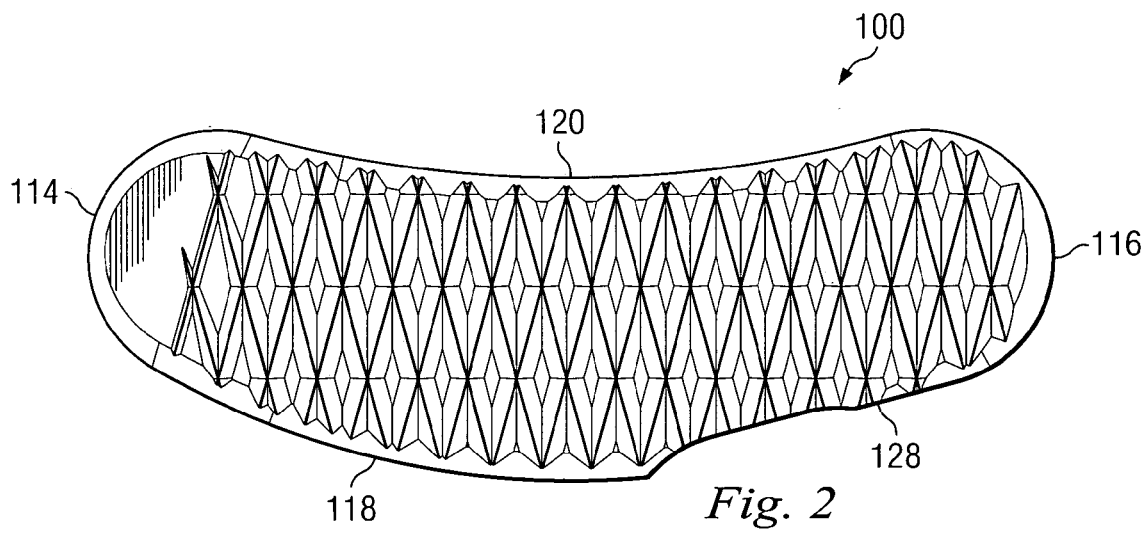
FIG. 2 is a bottom view of the implant of FIG. 1.
Figure 3:
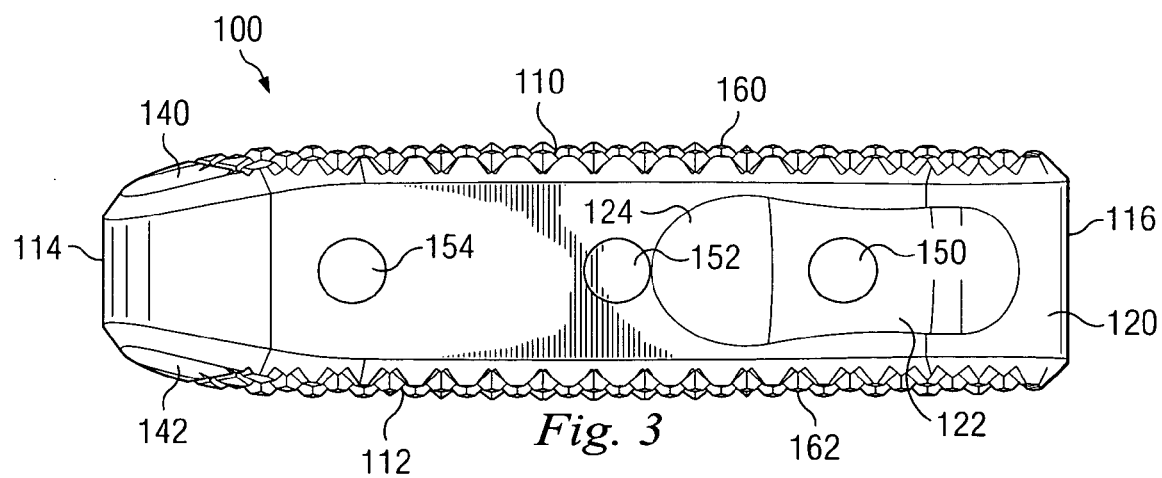
FIG. 3 is a side view of the implant of FIG. 1.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modifications in the described devices, instruments, methods and any further application of the principles of the invention as described herein are contemplated as would normally occur to one skilled in the art to which the invention relates.

Referring now to FIG. 1, there is shown a perspective view of an implant according to one aspect of the present invention. As shown more fully in FIGS. 1-5B, implant 100 includes an upper surface 110 and an opposing lower surface 112; each configured for contact with and/or placement in close approximation to the bone of adjacent upper and lower vertebrae, respectively. Implant 100 includes a leading end 114 and an opposite trailing end 116. Extending between the leading end 114 and the trailing end 116 is an anterior sidewall 118 having a substantially convex shape as it extends between the leading and trailing ends. An opposing posterior sidewall 120 having a substantially concave shape extends between the leading and trailing ends. Upper surface 110 includes a plurality of projections 160. In a similar manner, lower surface 112 includes a plurality of projections 162. Projections 160 and 162 are adapted for engaging bone to maintain the relative position of the implant 100 in the disc space between adjacent vertebrae. In the illustrated embodiment, anterior sidewall 118 and posterior sidewall 120 have a height extending between the upper and lower surfaces that is generally uniform across a majority of the implant. It is contemplated that the height of implant 100 will be selected to substantially maintain the height of an at least partially restored disc space between two adjacent vertebrae. Further, although not illustrated, it is contemplated that the height of the implant 100 may be formed to change from the anterior to posterior direction and to change from leading end 114 to trailing end 116. It will be appreciated that the height of the implant can be configured to substantially match the naturally occurring surfaces of the vertebral endplate and spacing of a restored height. Alternatively, implant 100 may be formed to match a disc space prepared to a desired space by bone removed from one or both of the endplates adjacent to disc space. Adjacent leading end 114, the height of the implant is reduced as tapered leading surface 140 transitions between tip 114 and upper surface 110. In a similar manner, lower surface 112 transitions along bottom leading tapered surface 142 as it approaches leading end 114.

Implant 100 includes a tool engagement configuration 128 adjacent trailing end 116. This provides the implant with a tapered tip to ease insertion. Tool engagement configuration 128 includes a cavity 122 formed on posterior sidewall 120. Cavity 122 has a substantially concave inner surface. Adjacent the trailing end 116, cavity 122 has a concave surface with a substantially uniform arcuate shape. As concave cavity 122 extends toward leading end 114, transition surface 124 blends the concave recess toward the substantially planar wall 120. As shown in more detail in FIG. 5B, cavity 122 is formed to have a surface that extends along the axis S2. There is a transition portion 123 immediately adjacent trailing end 116 adapted to initially engage an insertion arm and move it towards partial alignment with axis S2.

Figure 5A:
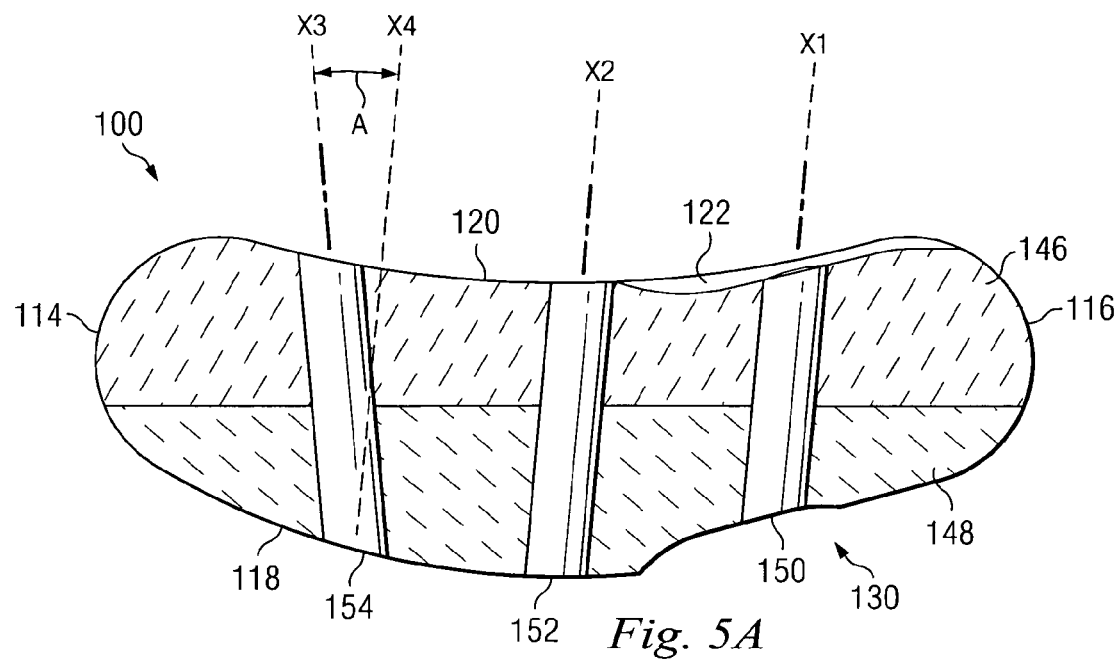
FIG. 5A is a cross-sectional view taken along line 5A-5A of FIG. 4.
Figure 5B:
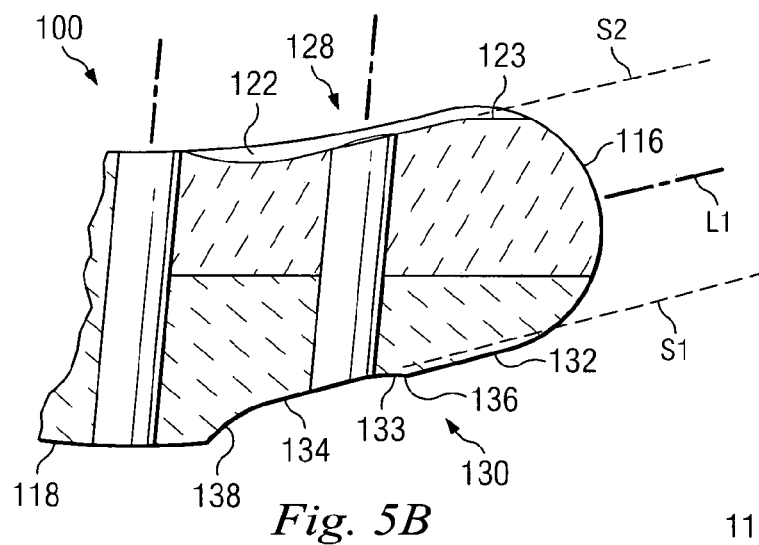
FIG. 5B is a partial cross-sectional view of the implant shown in FIG. 5A.
Figure 4:
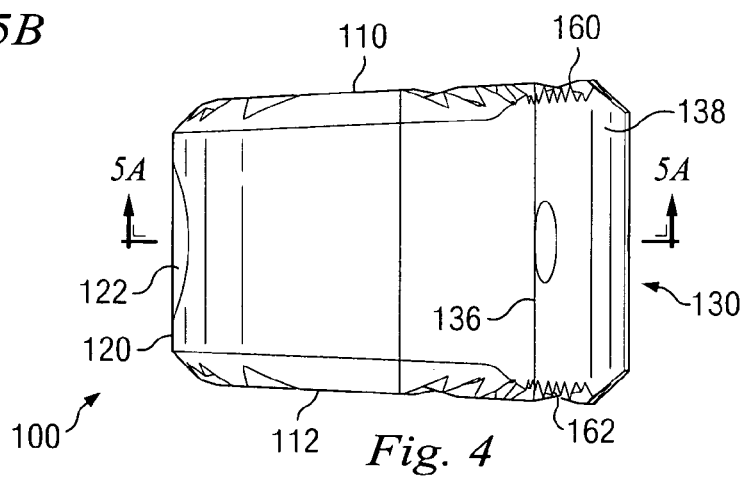
FIG. 4 is an end view of the implant of FIG. 1.

Opposite cavity 122, tool engagement configuration 128 includes a tool engagement surface 130 formed in and along anterior sidewall 118. In the illustrated embodiment, tool engagement surface 130 extends substantially between upper surface 110 and lower surface 112, and includes a plurality of individual planar surfaces. As best seen in FIG. 4, tool engagement surface 130 includes and intersects projections 160 on the upper surface 110 and projections 162 on the lower surface 112. As best illustrated in FIGS. 5A and 5B, tool engagement surface 130 includes a first planar surface 132, a second substantially planar and parallel surface 134 and a transition surface 133 extending between stepped surfaces 134 and 132. Where transition surface 133 intersects planar surface 132, a shoulder 136 is formed. Planar surface 134 extends to transition surface 138 which then joins it to sidewall 118. In the illustrated embodiment, second planar surface 134 extends along an axis S1. In the illustrated embodiment the tool engagement configuration 128 of implant 100 defines a longitudinal axis L1. Tool engagement surface 134 extends along axis S1 that is in substantial parallel alignment with axis L1. In contrast, tool engagement surface 122 extends along axis S2 that is offset from axis L1 and S1. In the illustrated embodiment S2 is offset from S1 by an angle of less than 5 degrees, preferably between 1 and 3 degrees, such that as surface 122 extends from distal end 116 toward leading end 114 the distance, the thickness of the implant, between surface 122 and surface 134 increases.

In the embodiment illustrated in FIGS. 1-5B, implant 100 is formed of two pieces of bone. As best seen in FIG. 5A, implant 100 is formed of a first bone portion 146 and second bone portion 148. These bone portions are held together by bone pins 150, 152 and 154. In the illustrated embodiment, bone pins 150 and 152 extend through bone portions 146 and 148 in a pair of bores extending along longitudinal axis X1 and longitudinal axis X2, respectively. Longitudinal axis X1 is substantially parallel to longitudinal axis X2. Pin 154 extends within a bore passing through bone portion 148 and 146 along a longitudinal axis X3. For reference, an axis X4 parallel to axis X2 is illustrated. In the illustrated embodiment, longitudinal axis X3 is offset with respect to longitudinal axis X4 by an angle A. Although many alternative angles may be used, in the illustrated embodiment angle A is between 5 and 10 degrees. It will be appreciated that providing joining pins 154 and 152 at a non-parallel, skew orientation, inhibits separation of bone portion 146 from bone portion 148 since there is not a single direction of travel along all of the axes of all the joining pins.

Referring now to FIGS. 6 and 7, there is shown an insertion tool in accordance with another aspect of the present invention. Insertion tool 200 includes a body 210 having a fixed handle 212 and an elongated shaft 214. Formed within an elongated shaft 214 is an elongated channel 215. Inserter 200 further includes a moveable shaft 216 having an elongated projection 217 sized and shaped to be slidably received within longitudinal channel 215. Inserter 200 includes a moveable lever 218 joined to body 210 by pivot pin 220 and pivotally joined (not shown) to movable shaft 216. It will be understood that movement of lever 218 about pin 220 will actuate moveable shaft 216 in a longitudinal direction such that projection 217 slides longitudinally within channel 215. In the illustrated embodiment, implant inserter 200 includes a distal end having reduced cross-sectional portion 226. The reduction in cross-sectional area is achieved by chamfered surface 222 on moveable shaft 216 and a similar chamfered surface 224 on fixed shaft 214. Although not shown, it will be understood that similar chamfered surfaces appear on the opposite sides of both the fixed shaft 214 and the moveable shaft 216.

Figure 8A:
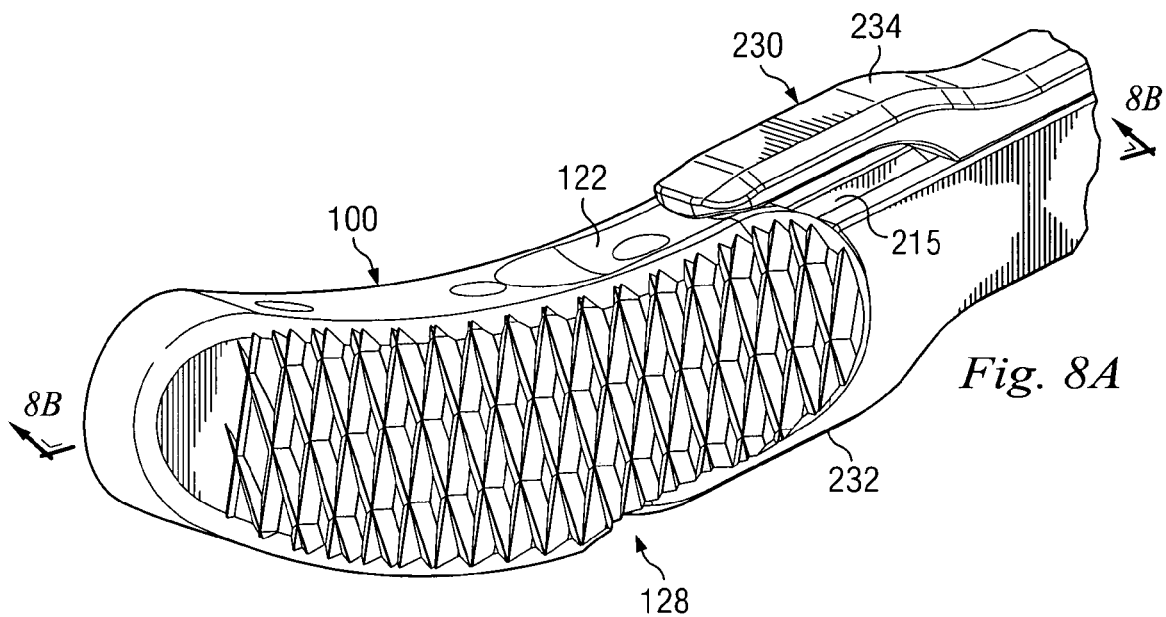
FIG. 8A is a partial perspective view of the implant of FIG. 1 partially engaged with the inserter of FIG. 6.
Figure 8B:
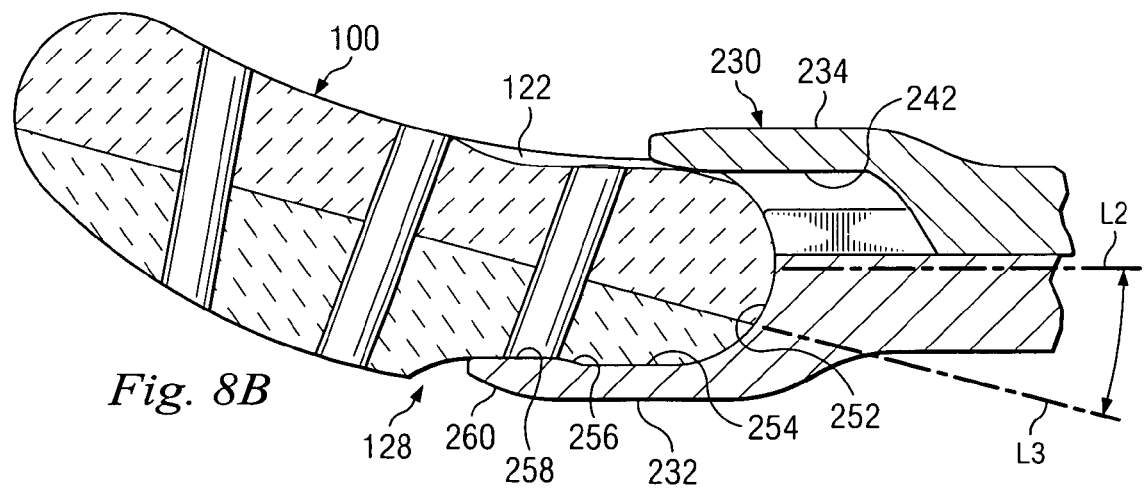
FIG. 8B is a partial cross-sectional view of the implant and insertion tool combination of FIG. 8A taken along section line 8B-8B.

Implant inserter 200 includes implant gripping end 230 defining an implant receiving channel 236 configured and adapted to receive a suitable implant. Implant gripping end 230 is formed of a fixed arm 232 extending from fixed shaft 214. In a similar manner and cooperating with the fixed arm 232, implant gripping end 230 further includes a sliding arm 234 extending from moveable shaft 216. Sliding arm 234 includes an internal surface 240 configured for implant engagement. In the illustrated embodiment, internal surface 240 includes a convex projection 242 extending along at least a portion of the length thereof. Convex projection 242 projects from flat surface 244 such that the implant engaging surface includes both a projection as well as a flat portion. The trailing end portion of internal surface 240 is curved to mate with a curved portion of an implant. Referring also to FIGS. 8A and 8B, fixed arm 232 includes an internal surface 250 adapted and configured for engagement with an implant. Internal surface 250 includes a curved surface 252 for engaging a trailing end of an implant, a substantially planar surface 254 extending between the lateral edges of the implant inserter, a curved surface 256 forming a shoulder and an inwardly facing projection 258. In the illustrated embodiment, inwardly facing projection 258 extends along a plane substantially parallel to the longitudinal axis L2 of gripping end 230. The external surface of fixed arm 232 includes a leading tapered tip 260 to minimize trauma during insertion.

As shown in FIG. 8B, convex surface 242 extends parallel to longitudinal axis L2 and is thereby parallel to opposing surface 258. The moveable arm 216 is attached to fixed arm 214 such that it slides in a direction parallel to the longitudinal axis L2.

As shown more fully in FIGS. 8A and 8B, implant 100 is partially received in channel 236 in gripping end 230. The implant 100 is particularly adapted for unilateral placement in the disc space between two adjacent vertebrae. When engaged with inserter 200, the longitudinal axis L3 of the implant is offset from the longitudinal axis L2 of the insertion tool. However, the longitudinal axis L1 of the implant tool engagement portion 128 is substantially aligned with axis L2. As shown in FIG. 8B, moveable arm shaft 234 has been axially displaced proximally along the longitudinal axis L2 of the implant inserter 200 so that it is in the disengage position. As illustrated, convex projection 242 is axially spaced from concave recess 122 formed in implant 100. In this position, implant inserter 200 may be axially removed from engagement with implant 100. It will be appreciated that projection 258 may slide over shoulder 136 in an axial direction to fully and completely disengage the implant from the implant inserter. Inserter axis L2 is substantially offset from axis S2 of concave recess 122 when projection 258 is received and positioned against surface 134. In a preferred aspect, the difference between axis L2 and axis S2 is less than approximately 5 degrees. Still further, it is contemplated that the axis may have between one and three degrees of offset relationship.

Figure 9A:
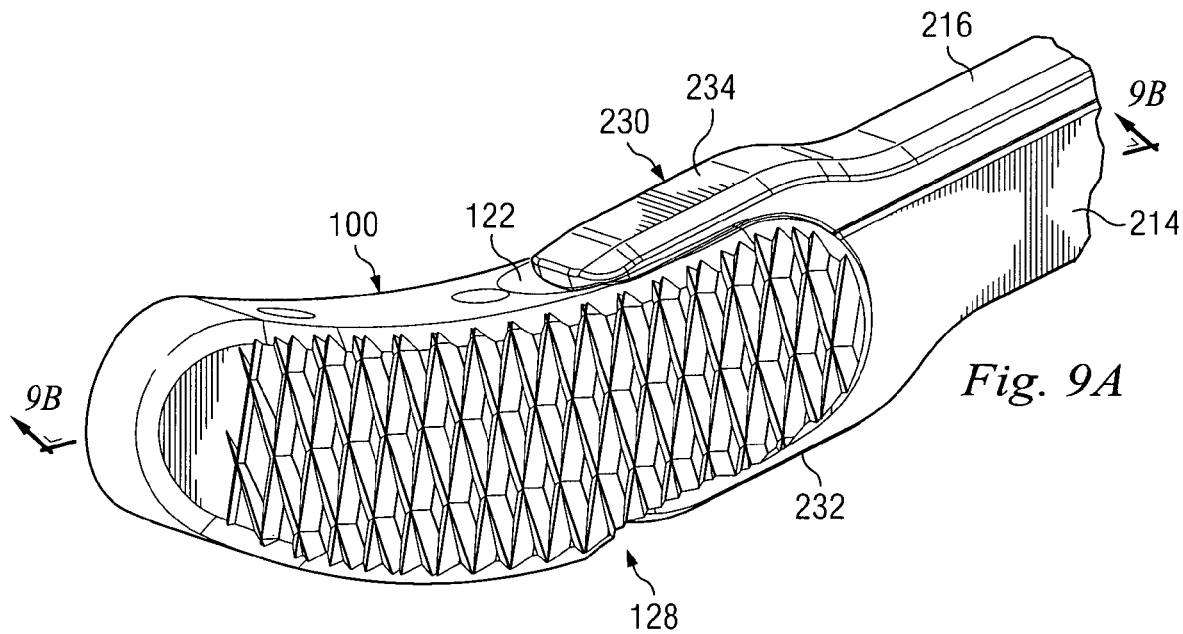
FIG. 9A is a partial perspective view of the implant and insertion tool of FIG. 8A shown in a gripping position.
Figure 9B:
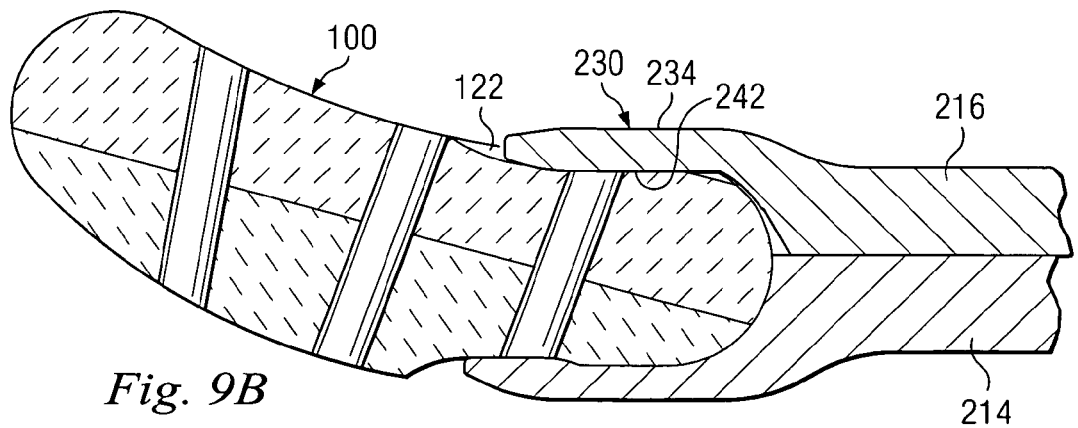
FIG. 9B is a partial cross-sectional view of the implant and inserter combination of FIG. 9A taken along section lines 9B-9B.

Referring now to FIGS. 9A and 9B, moveable shaft 216 has been moved distally longitudinally along the axis L2 of the implant inserter with respect to fixed shaft 214. Movement is caused by actuating lever 218 and moving it towards fixed handle 212. As the sliding arm 234 moves forward with respect to fixed arm 232, convex projection 242 is fully engaged and received within cavity 122. Given the offset relationship between the surface of convex projection 242 extending along axis L2 and convex cavity 122 extending along axis S2, continued axially advancement of sliding arm 234 grips and engages implant between the fixed arm 232 and sliding arm 234. In the illustrated embodiment, implant 100 is formed of bone. In this embodiment, it is contemplated that continued forward advancement of sliding arm 234 will result in at least some deformation of the material immediately adjacent to and forming the surface of cavity of 122 and/or the material adjacent to tool engaging surface 130. This deformation will be to conform the surface to the external shape of convex projection 242 and will provide an intimate mating engagement.

Implant 100 is removed from the gripping end 230 of implant inserter 200 by actuation of lever 218 away from fixed handle 212. In this manner, moveable shaft 216 is moved distally with respect to fixed shaft 214 by action of lever 218 away from fixed handle 212. In the illustrated embodiment, the axial displacement of gripping arm 234 with respect to gripping arm 232 allows the implant inserter 200 to be disengaged from implant 100. It will be appreciated, that the surgical access necessary to insert implant 100 while joined to implant inserter 200 does not need be increased in its perimeter or cross-sectional area to achieve the disengagement of the inserter from the implant.

Figure 10:
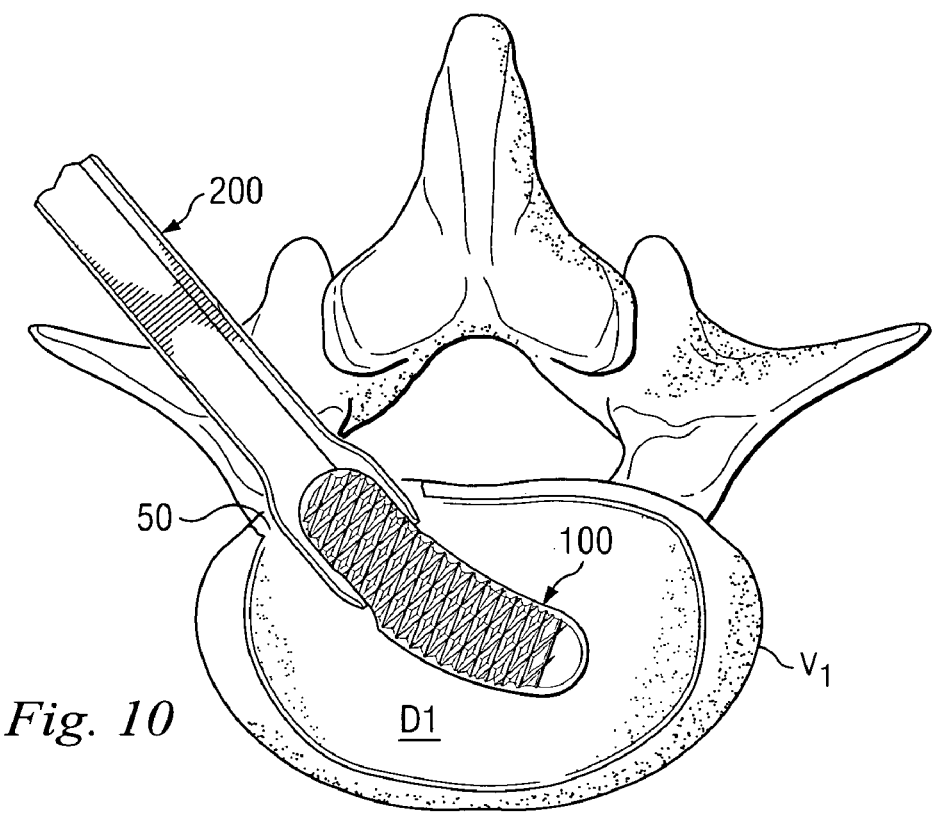
FIG. 10 shows the implant and insertion tool being positioned in the disc space between adjacent vertebrae.

Referring now to FIG. 10, implant 100 is shown engaged with implant inserter 200 and extending into the disc space D1 adjacent vertebra V1 through an opening 50 in the annulus. It will be appreciated, that the illustrated technique demonstrates a transforaminal approach to the disc space. While the illustrated embodiment of implant inserter and implant have been shown with reference to utilization in this type of technique, the present invention is not limited to a particular approach to the spine and the teachings and principles of the present invention may be utilized for other surgical techniques. It will be appreciated, that implant inserter 200 may be disengaged, without rotational movement or outward expansion of inserter engaging components, from implant 100 to leave the implant in the disc space D1 to provide spacing and permit the body to fuse the adjacent vertebrae. Moreover, the inserter may be used with a variety of implants, including but not limited to, bone grafts, spacers, nucleus replacements, artificial discs or any other spinal implant.

Figure 11:
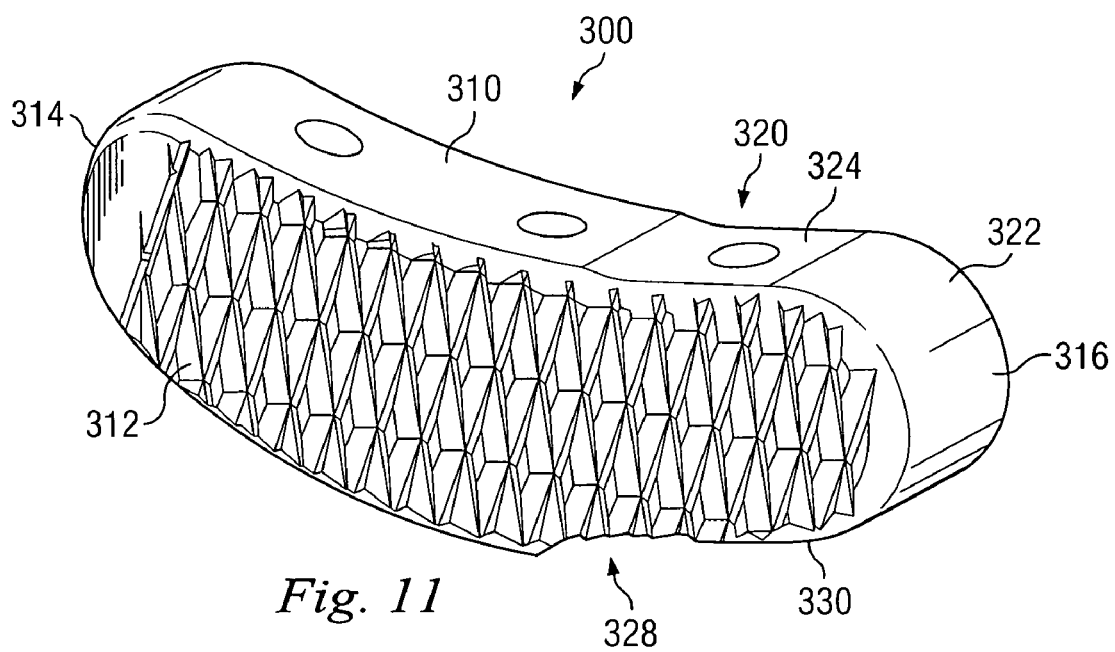
FIG. 11 is a perspective view of a further embodiment of an interbody spacer according to the present invention.

Referring now to FIG. 11, there is shown an alternative embodiment of an implant according to another aspect of the present invention. Implant 300 has many similarities to the implant 100 described above. For example, implant 300 includes a lower surface 312 and an opposite upper surface (not shown). These surfaces are joined by a posterior side wall 310 and an opposite anterior side wall (not shown). These sidewalls extend between leading end 314 and trailing end 316. Adjacent to trialing end 316, there is a tool engagement portion 328 defined by anterior tool engaging configuration 330, substantially identical to anterior tool engaging configuration 130 of implant 100 and an opposing posterior tool engaging configuration 320. Engaging configuration 320 includes a curved wall 322 adjacent the trialing end 316 that transitions to engagement wall 324. Engagement wall 324 is a substantially planar surface extending between lower surface 312 and the opposite upper surface. As described with respect to implant 100, this surface is formed at a slight angle or taper with respect to anterior tool engaging configuration 330 such that the implant increases slightly in thickness from trailing end 316 toward leading end 314 in the tool engaging portion 328.

Referring now to FIG. 12, there is shown an implant insertion tool 400 matingly engaged with implant 300. Insertion tool 400 is similar in most respects to the embodiment illustrated in FIG. 6. Insertion tool 400 includes a fixed gripping arm 432 and a slidable gripping arm 434. Slidable gripping arm 434 includes a concave internal surface 440 adapted to engage the distal curved wall 322 of the implant 300. Further, slidable gripping arm 434 includes a substantially planar implant engagement surface 444 configured for engagement with engagement wall 324 of the implant 300. As previously described with respect to the embodiments shown in FIGS. 1-10, the plane of implant engaging surface 444 extends parallel to the longitudinal axis of the inserter and the distal end of the implant. However, it is non-parallel with respect to the plane of engagement wall 324. In a preferred embodiment, the engagement wall 324 extends at an angle of less than 5 degrees with respect to the other elements of engagement. As previously described, as the slidable arm 434 is moved distally along the longitudinal axis toward the implant 300, the difference in the angulation of surfaces 444 and 324 tends to cause a tight gripping of the implant. It will be understood that as arm 434 advances longitudinally, the inserter will tend to forcibly compress the implant material between the two gripping arms 434 and 432. It is contemplated that for implants formed of bone, synthetic bone substitutes, coral and other similar materials, the implant walls will tend to deform inwardly at least in part perpendicular to the longitudinal axis in response to the pressure exerted by movement of the gripping arm 434 in an axial direction. The engagement of the inclined tool engagement surface 434 with the flat insertion tool surface 444 transforms at least a portion of the axial movement of the gripping arm into a gripping force perpendicular to the longitudinal axis.

A further embodiment of an implant 500 in combination with an implant insertion tool 600 is shown in FIGS. 13A-14B. Implant 500 has a leading end 502 and an opposite trailing end 504 spaced by a posterior side wall 506 and an opposite anterior portion 508. The implant includes a tool engaging configuration 510 disposed adjacent the trailing end 504. The tool engaging configuration 510 includes a posterior slot 512 formed in posterior wall 506 and an opposing anterior slot 514 formed in the wall of the anterior portion 508.

FIG. 13B illustrates implant 500 in combination with the implant insertion tool 600. Implant insertion tool 600 includes a handle 610, elongated external shaft 612 and an implant gripping end 630. As illustrated in FIG. 13B, the distal portion of elongated shaft 612 is reduced in diameter to form reduced diameter portion 614. Gripping end 630 includes a stationary first arm 632 spaced from a second stationary arm 634 defining an implant socket. First arm 632 is sized narrower than the height of implant 500 from top bone engaging surface 509 to the bottom bone engaging surface (not shown) such that it may be received within posterior slot 512. In a similar manner, second arm 634 is sized narrower than the height of the implant such that it may be received in anterior slot 514. First arm 632 includes an interior surface having a substantially planar implant engaging surface 636. Second arm has an interior surface having a substantially planar distal surface 642 configured for engagement within slot 514 and a substantially planar proximal surface 640 extending at an angle with respect to surface 642, and adapted for engaging an exterior trailing surface of implant 500. Extending between planar surface 636 and planar surface 640 is a concave surface 638. An aperture 644 extends through surface 640.

Figure 14A:
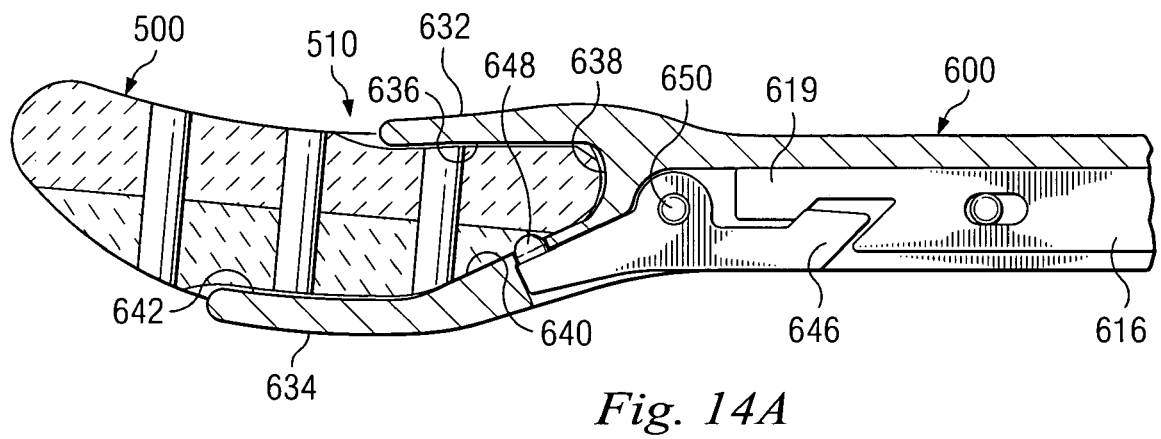
FIG. 14A is a partial cross-sectional view of the implant and inserter combination of FIG. 13B taken along section line 14A-14A.
Figure 14B:
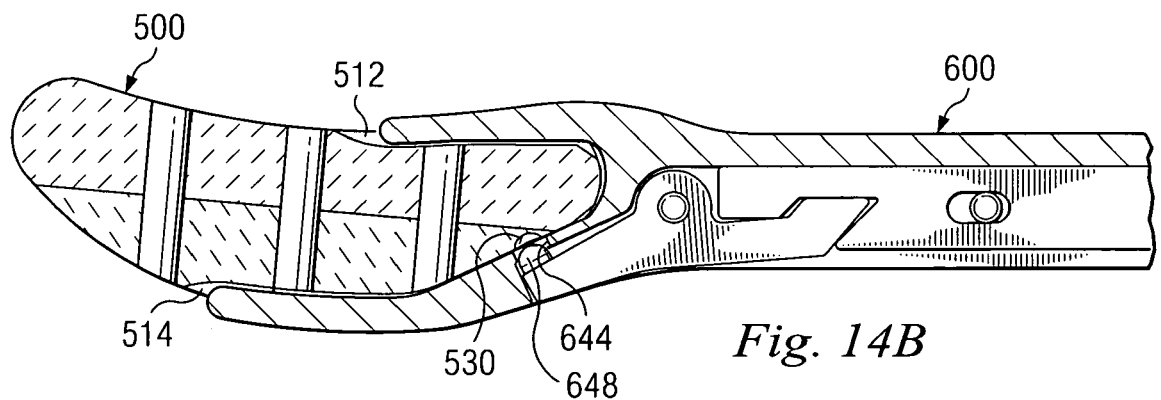
FIG. 14B shows the embodiment of FIG. 14A with the locking mechanism in an open position.

As best illustrated in FIGS. 14A and 14B, an internal shaft 616 extends within external shaft 612 between handle 610 and gripping end 630. A lever 620 is mounted within handle 610 and pivotally connected to the proximal end 617 of internal shaft 616. Actuation of lever 620 cause internal shaft 616 to move axially within external shaft 612. The distal end 619 of internal shaft 616 is coupled to a pivot arm 646. Pivot arm 646 is joined to external shaft 612 by a pivot pin 650. Opposite the connection to distal end 619, pivot arm 646 defines a ball projection 648 configured for extension through aperture 644 into the implant socket when in the locking position shown in FIG. 14A. As the ball projection 648 extends through aperture 644 it is received in detent 530 formed in implant 500. It will be appreciated that this connection between ball 648 and detent 530 securely holds the implant 500 from axial displacement from the insertion tool. The engagement between the internal surfaces of the gripping end 630 and the implant allows the transmission of force from the insertion tool in all ranges of motion. As shown in FIG. 14B, axial displacement of internal shaft 616 causes pivot arm 646 to rotate and moves ball 648 into aperture 644 and out of detent 530. In this unlocked position, insertion tool 600 may be disengaged from implant 500. It will be appreciated that there is no rotation of components about the longitudinal axis required for disengagement. Further, the cross-sectional dimensions of the insertion tool from the external shaft 612 to the gripping end 630 are unchanged. In this manner, no enlargement of the surgical exposure is needed to remove the insertion tool from the patient during surgery.

The bone engaging surface 509 of implant 500 includes a plurality of generally diamond shaped projections 520. Diamond shaped projection 520 includes a leading edge 522, a trailing edge 524, a posterior edge 526 and an anterior edge 528. The lengths of the leading edge 522 and the posterior edge 524 are substantially greater that the lengths of the posterior edge 526 and the anterior edge 528. In this configuration, the diamond projection 520 is oriented in substantial alignment with the longitudinal axis of the implant 500 and in the direction of insertion between the leading end 502 and the trailing end 504. During insertion, the diamond projection 520 presents the narrowest dimension to the adjacent bone thereby promoting forward advancement. In contrast, the widest portion of the diamond projection 520 is presented in the posterior to anterior direction. Thus, the diamond projection presents greater resistance to movement in the posterior to anterior direction than resistance to movement in the direction of insertion from leading to trailing end. It will be understood that this design may assist the surgeon in positioning the implant in the direction of insertion while the implant surface configuration resists forces applied that tend to urge it off the line of insertion chosen by the surgeon. Further, the illustrated knurling pattern has a greater resistance to dislodgement in the posterior to anterior direction than a non-oriented diamond pattern of uniform dimensions.

Figure 15A:
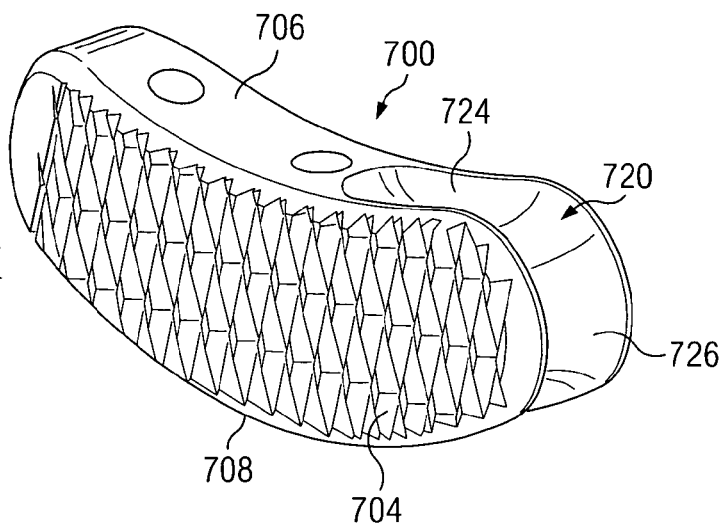
FIG. 15A is a perspective view of an implant according to another embodiment of the present invention.
Figure 15B:
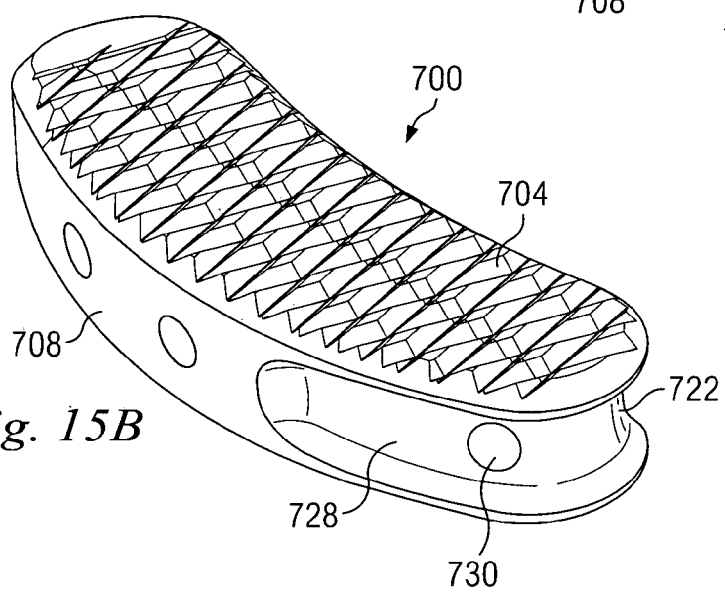
FIG. 15B is an alternative perspective view of the implant of FIG. 15A.

Referring now to FIGS. 15A and 15B, there is shown an implant 700 according to a further embodiment of the present invention. Implant 700 has many of the same features of the implant 500 previously described. However, adjacent trialing end 704 there is disposed an alternative insertion tool engagement feature 720. Engagement feature 720 includes a continuous groove 722 extending from and into the posterior side wall 706 to and at least partially along the anterior side wall 708. Groove 722 has a substantially uniform convex surface recessed within the material of implant 700. The posterior portion 724 of groove 720 communicates with and transitions into a trailing end portion 726. The groove 720 continues from the trailing end portion 726 to an anterior portion 728. Disposed within the anterior portion 728 is a detent 730.

Figure 16:
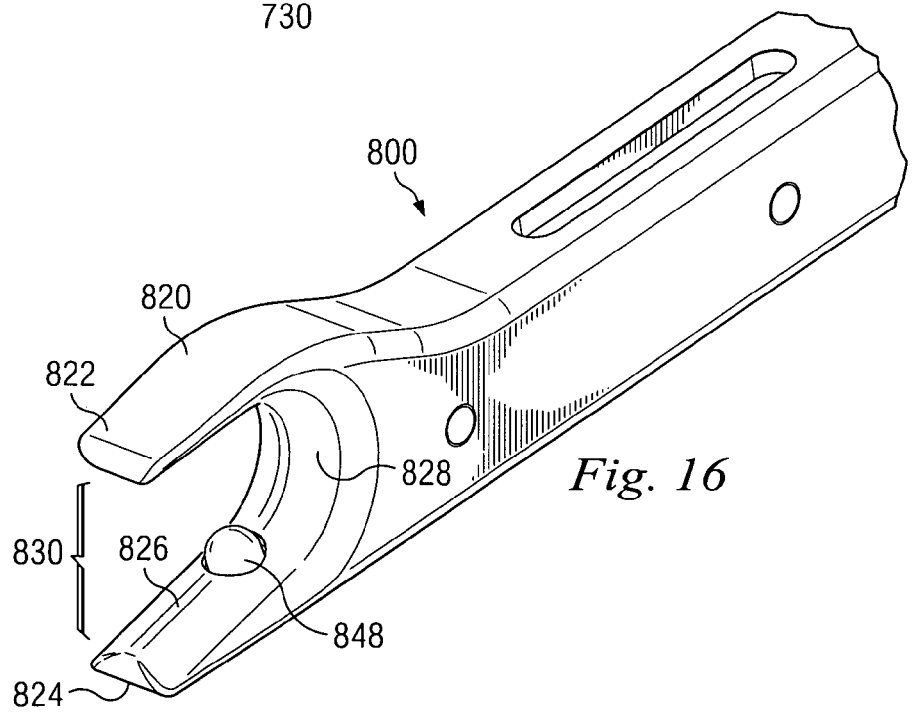
FIG. 16 is a partial perspective view of the gripping end of an implant insertion tool according to a further embodiment of the present invention.
Figure 17:
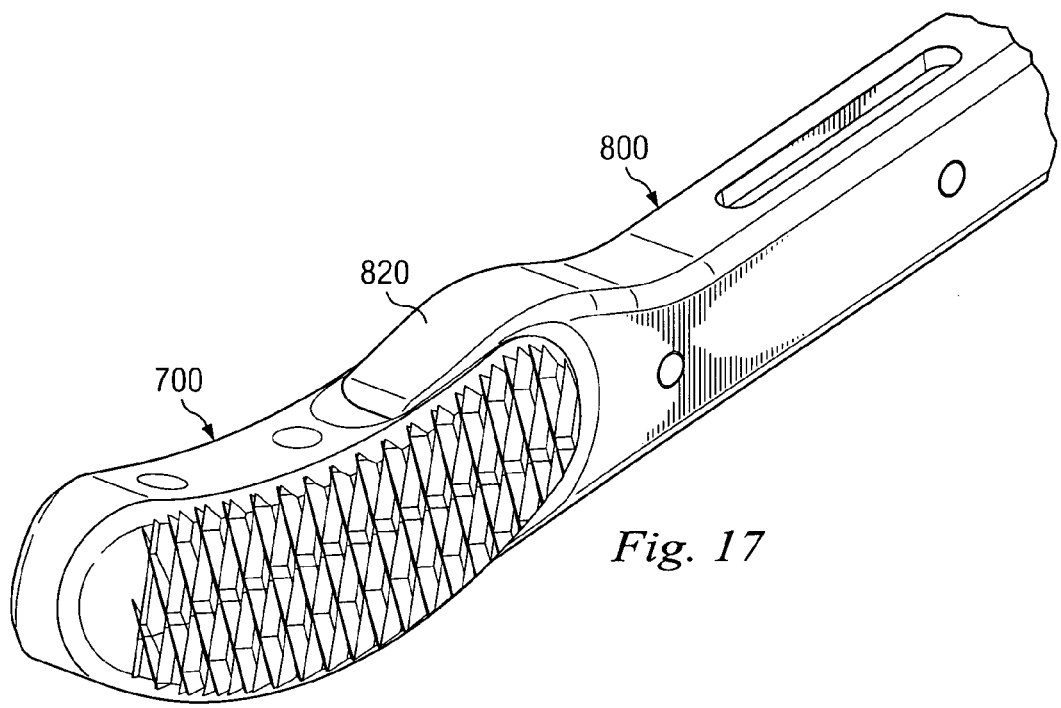
FIG. 17 is a partial perspective view of the implant of FIG. 15A in combination with the insertion tool of FIG. 16.

FIG. 16 illustrates a partial perspective view of an insertion tool 800 with a gripping end 820. It will be appreciated that the proximal portion of insertion tool 800 is not illustrated and may be formed in a substantially identical fashion to that previously illustrated in FIG. 13B with respect to insertion tool 600. A posterior gripping arm 822 and an opposite anterior gripping arm 824 define a stationary implant receiving socket 830. In the illustrated embodiment, a substantially continuous convex surface 826 extends from side to side on the internal surface of gripping arms 822 and 824 facing the receiving socket 830. The convex surface 826 extends from the distal end of gripping arm 822, along the intermediate portion 828 and along gripping arm 824. Although a continuous surface is not required for the present invention, it is provided in the present embodiment to increase the surface area contact for the transmission of implantation forces and provide a smooth surface contact to inhibit the formation of stress risers in the implant that may lead to fracture. As with the insertion tool 600, a ball 848 configured for engagement with detent 730 on the implant 700, projects through an aperture in gripping arm 824. The mechanism for movement of the ball 848 may be substantially as previously described with respect to the insertion tool 600. FIG. 17 illustrates the implant 700 matingly engaged with insertion tool 800. It will be appreciated that the convex curvature of convex surface 826 is configured to closely match the concave surface of groove 720.

Figure 18A:
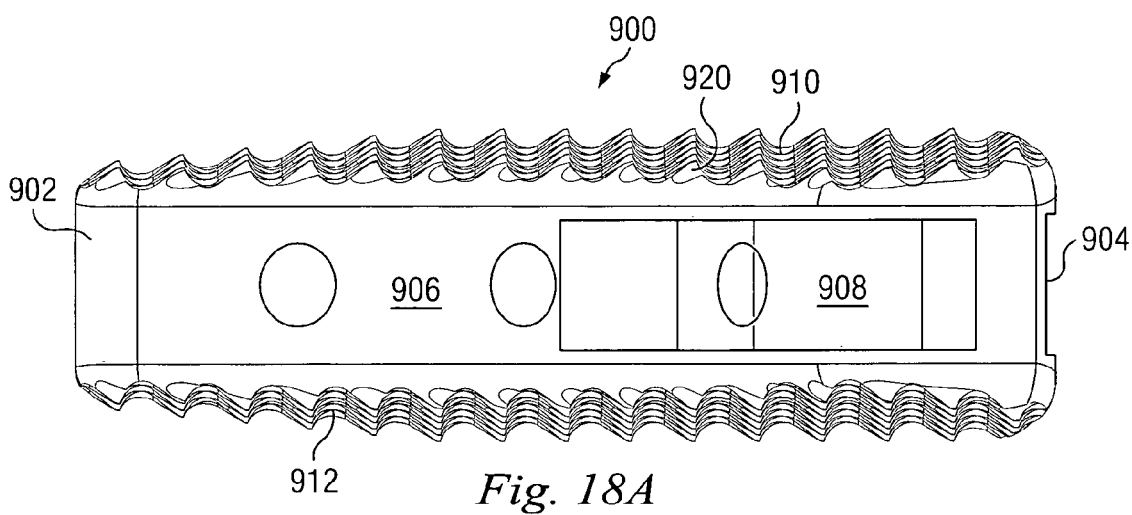
FIG. 18A is a side view of a further embodiment of an implant according to the present invention.
Figure 18B:
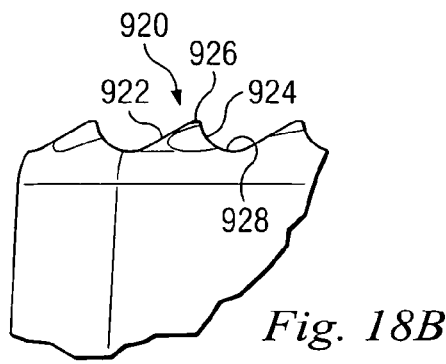
FIG. 18B is an enlarged partial side view of a surface projection formed on the implant of FIG. 18A.

Referring now to FIGS. 18A and 18B, there is shown a further implant according to another aspect of the present invention having an alterative bone engaging surface configuration. Implant 900 has a leading end 902 and an opposite trailing end 904. The implant 900 has an upper bone engaging surface 910 and a lower bone engaging surface 912 spaced from each other by side wall 906. An insertion tool engaging configuration is disposed adjacent trailing end 904. Each surface has a series of projections 920 configured for engagement with the bone of adjacent vertebrae upon insertion into an intervertebral disc space. Referring to the enlarged view shown in FIG. 18B, each projection 920 has a leading surface 922 and a trailing surface 924. A peak 926 is formed where the leading surface 922 and trailing surface 924 intersect. In a preferred aspect, the peak 926 is a relatively sharp projection. It will be appreciated that with materials having greater strength, the trailing surface may be formed to at least in part undercut the leading surface. The side view of each projection 920 has the form of a shark fin with the leading edge 922 being a generally straight surface angled toward the trailing end and the trailing edge 924 being an at least partially concave surface. The trough 928 between each projection 920 is a radiused concave surface.

Figure 19A:
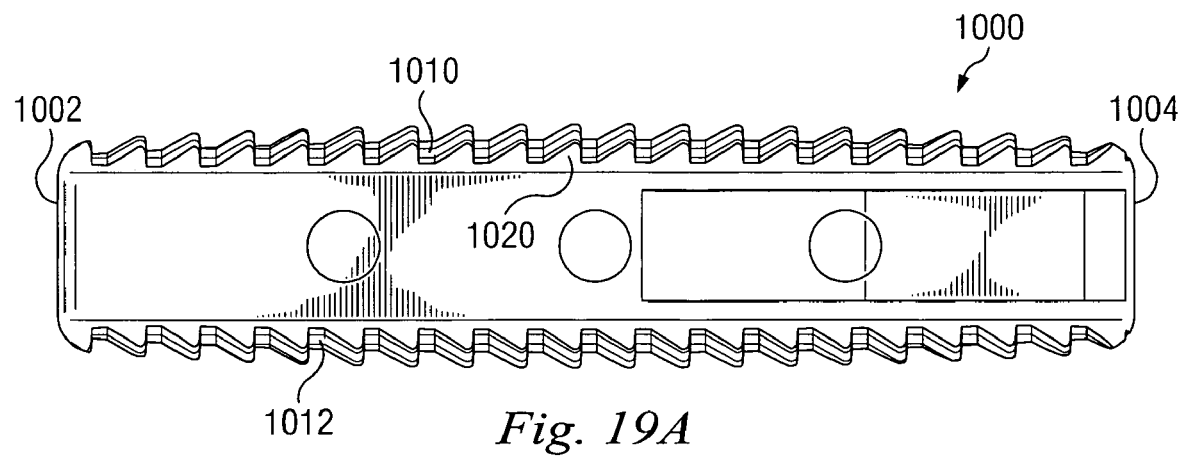
FIG. 19A is a side view of still a further implant according to another embodiment of the present invention.
Figure 19B:
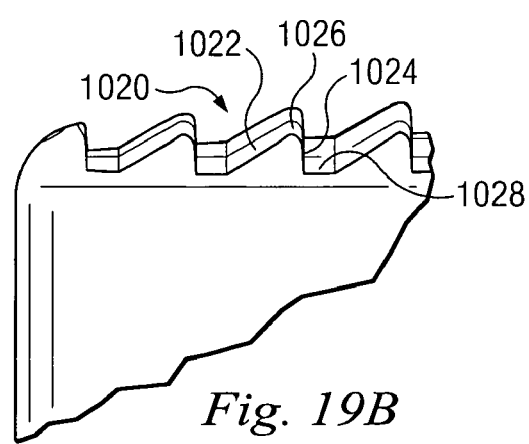
FIG. 19B is an enlarged partial side view of a surface projection of the implant of FIG. 19A.

A still further alternative surface configuration is illustrated in FIGS. 19A and 19B. Implant 1000 has a leading end 1002 and an opposite trailing end 1004. The implant 1000 has an upper bone engaging surface 1010 and a lower bone engaging surface 1012. Each surface has a series of projections 1020 configured for engagement with the bone of adjacent vertebral endplates upon insertion into an intervertebral disc space. Referring to the enlarged view shown in FIG. 19B, each projection 1020 has a leading surface 1022 and a trailing surface 1024. A peak 1026 is formed where the leading surface 1022 and trailing surface 1024 intersect. In a preferred aspect, the peak 1026 is rounded to form a relatively blunt projection. The cross section side view of each projection 1020 has the form of a ramp with the leading edge 1022 being a generally straight surface angled toward the trailing end and the trailing edge 1024 being a surface that extends generally perpendicular to the longitudinal axis of the implant 1000. The trough 1028 between each projection 1020 is a substantially planar surface generally parallel to the longitudinal axis of the implant.

The implants described above may be formed of any material suitable for implantation. The insertion tools described above are generally formed of medical grade materials suitable for such applications, including stainless steel and titanium. In one aspect, the implant may be formed of a material that is softer or more brittle than the material of the inserter such that the implant may at least partially yield to the gripping force applied by the gripping end of the inserter. For example, the inserter may be formed of stainless steel and the implant formed of cortical bone. Alternatively, the implant may be formed of a resorbable polymer, such as PLDLA or similar compounds. While not exhaustive and without limitation to the use of other implant materials, examples include: hydroxyappetite, biphasic calcium, coral, ceramic compounds, composite bone, allograft, autograft and xenograft.

The implants 100 and 300 described above illustrate the offset angled surface on the implant on the posterior side. This description has been made without limitation and for the purposes of illustration, it being contemplated that such offset surfaces can be fashioned in any location on the implant tool engaging end or may be carried by the gripping arms of the inserter. In a similar manner, the location of the detent in implants 500, 700, 900 and 1000 is for the purpose of illustration only is not intended to limit the placement or position at other locations on the implant. Still further, it is contemplated that alternative recess and projection configurations may be utilized in place of the ball and detent structures illustrated. For example, but without limitation, the recess shape may be elliptical, rectangular, cylindrical, square, pyramid, conical, trapezoidal or triangular with an at least partially mating projection on the inserter that can be received within the recess. Still further, the recess in the implant may be formed by movement of a relatively sharp projection from the inserter that at least partially penetrates or engages the surface of the implant. While singular projections and recesses have been disclosed, it is also contemplated that multiple recesses and projections may be utilized to retain the implant in the implant socket of the inserter.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An apparatus comprising:
an implant for positioning at least partially in a disc space between two adjacent vertebrae, the implant comprising:
an upper bone engaging surface for engaging at least a portion of an upper vertebral body and an opposite lower bone engaging surface for engaging at least a portion of a lower vertebral body;
a first end surface extending between said upper and lower bone engaging surfaces and an opposite second end surface extending between said upper and lower bone engaging surfaces; and
a first side surface extending between said upper and lower bone engaging surfaces and an opposite second side surface extending between said upper and lower bone engaging surfaces;
the first and second side surfaces and the first end surface defining an insertion tool engagement configuration for mating with an insertion tool, said first side surface including a first generally planar surface portion extending substantially parallel to a longitudinal axis of the implant and spaced a first distance from the longitudinal axis, a second generally planar surface portion extending substantially parallel to the longitudinal axis and spaced a second distance from the longitudinal axis, the second distance being less than the first distance, a generally planar transition surface portion extending between the first surface portion and the second surface portion at an oblique angle with respect to the longitudinal axis, the intersection of the transition surface portion and the first surface portion defining a shoulder, said second side surface including a substantially planar surface portion extending at an oblique angle with respect to the longitudinal axis such that a width of the implant between the first generally planar surface portion of the first side surface and the substantially planar surface portion of the second side surface in a direction substantially perpendicular to the longitudinal axis increases as the substantially planar surface portion of the second side surface extends away from the first end surface; and
an insertion tool for engaging the insertion tool engagement configuration of the implant, the insertion tool comprising:
a first elongated shaft extending along a tool axis and having an elongated channel formed therein;
a second elongated shaft movably positioned within the channel of the first elongated shaft, the second elongated shaft movable along the tool axis with respect to the first elongated shaft;
the first and second elongated shafts defining an implant gripping mechanism for engaging the implant.

2. The apparatus of claim 1, wherein the implant gripping mechanism includes a fixed arm associated with the first elongated shaft and a sliding arm associated with the second elongated shaft, the sliding arm being movable with respect to the fixed arm along the tool axis between a first position for receiving and releasing the implant and a second position for engaging the implant.

3. The apparatus of claim 2, wherein the insertion tool further comprises an actuator for selectively moving the second elongated shaft relative to the first elongated shaft to move the sliding arm between the first position and the second position.

4. The apparatus of claim 2, wherein the fixed arm is shaped to engage with the first generally planar surface portion, the generally planar transition surface, and the second generally planar surface portion of the first side surface and wherein the sliding arm is shaped to engage with the substantially planar surface portion of the second side surface.

5. The apparatus of claim 2, wherein the tool axis extends substantially parallel to the longitudinal axis of the implant when the insertion tool is engaged with the implant.

6. An apparatus comprising:
an implant for positioning at least partially in a disc space between two adjacent vertebrae, the implant comprising:
an upper bone engaging surface for engaging at least a portion of an upper vertebral body and an opposite lower bone engaging surface for engaging at least a portion of a lower vertebral body;
a first end surface extending between said upper and lower bone engaging surfaces and an opposite second end surface extending between said upper and lower bone engaging surfaces; and
a first side surface extending between said upper and lower bone engaging surfaces and an opposite second side surface extending between said upper and lower bone engaging surfaces;
the first and second side surfaces and the first end surface defining an insertion tool engagement configuration for mating with an insertion tool, said first side surface including a first surface portion extending substantially parallel to a longitudinal axis of the implant, a second surface portion extending substantially parallel to the longitudinal axis and spaced from the first surface portion, the second surface portion being positioned closer to the longitudinal axis than the first surface portion, a transition surface portion extending between the first surface portion and the second surface portion, the intersection of the transition surface portion and the first surface portion defining a shoulder, said second side surface including a substantially planar surface portion extending at an oblique angle with respect to the longitudinal axis such that a width of the implant between the first generally planar surface portion of the first side surface and the substantially planar surface portion of the second side surface in a direction substantially perpendicular to the longitudinal axis increases as the substantially planar surface portion of the second side surface extends away from the first end surface; and
an insertion tool for engaging the insertion tool engagement configuration of the implant, the insertion tool comprising:
a first elongated shaft extending along a tool axis and having an elongated channel formed therein;
a second elongated shaft movably positioned within the channel of the first elongated shaft, the second elongated shaft movable along the tool axis with respect to the first elongated shaft;
the first and second elongated shafts defining an implant gripping mechanism for engaging the implant;
wherein the implant gripping mechanism includes a fixed arm associated with the first elongated shaft and a sliding arm associated with the second elongated shaft, the sliding arm being movable with respect to the fixed arm along the tool axis between a first position for receiving and releasing the implant and a second position for engaging the implant, wherein the fixed arm includes:
a first engagement surface portion for engaging the first surface portion of the implant, the first engagement surface extending substantially parallel to the tool axis and spaced from the tool axis a first distance,
a second engagement surface portion for engaging the second surface portion of the implant, the second engagement surface portion extending substantially parallel to the tool axis and spaced from the tool axis a second distance less than the first distance, and
a third engagement surface portion for engaging the transition surface portion of the implant and extending between the first and second engagement surface portions,
wherein the implant gripping mechanism is configured to engage the implant such that engagement of the implant gripping mechanism with the implant prevents disengagement of the insertion tool from the implant along the longitudinal axis of the implant;
wherein the tool axis extends substantially parallel to the longitudinal axis of the implant when the insertion tool is engaged with the implant; and
wherein the sliding arm of the insertion tool deforms at least a portion of the implant as the sliding arm is advanced along the tool axis causing the insertion tool to engage with the implant due to the increase in width of the implant between the first generally planar surface portion of the first side surface and the substantially planar surface of the second side surface increases as the substantially planar surface of the second side surface extends away from the first end surface.

7. An apparatus comprising:
an implant for positioning at least partially in a disc space between two adjacent vertebrae, the implant comprising:
an upper bone engaging surface for engaging at least a portion of an upper vertebral body and an opposite lower bone engaging surface for engaging at least a portion of a lower vertebral body;
a first end surface extending between said upper and lower bone engaging surfaces and an opposite second end surface extending between said upper and lower bone engaging surfaces; and
a first side surface extending between said upper and lower bone engaging surfaces and between said first and second end surfaces and an opposite second side surface extending between said upper and lower bone engaging surfaces and between said first and second end surfaces;
the first and second side surfaces and the first end surface defining an insertion tool engagement configuration for mating with an insertion tool, said first side surface including a first generally planar surface portion extending substantially parallel to a longitudinal axis of the implant, a second generally planar surface portion extending substantially parallel to the longitudinal axis and spaced from the first surface portion, the second generally planar surface portion positioned closer to the longitudinal axis than the first generally planar surface portion, a generally planar transition surface portion extending between the first surface portion and the second surface portion at an oblique angle relative to the longitudinal axis, the intersection of the transition surface portion and the first surface portion defining a shoulder, said second side surface including a substantially planar surface portion extending at an oblique angle with respect to the longitudinal axis such that a width of the implant between the first generally planar surface portion of the first side surface and the substantially planar surface of the second side surface in a direction substantially perpendicular to the longitudinal axis increases as the substantially planar surface of the second side surface extends away from the first end surface; and
an insertion tool for engaging the insertion tool engagement configuration of the implant, the insertion tool comprising:
a first elongated shaft extending along a tool axis and having an elongated channel formed therein;
a second elongated shaft movably positioned within the channel of the first elongated shaft, the second elongated shaft movable along the tool axis with respect to the first elongated shaft;
the first and second elongated shafts defining an implant gripping mechanism for engaging the implant, the implant gripping mechanism comprising:
a fixed arm associated with the first elongated shaft, the fixed arm comprising a first planar surface portion for engaging the first generally planar surface portion of the implant and a projection including a planar engagement surface for engaging the second generally planar surface portion of the implant; and
a sliding arm associated with the second elongated shaft, the sliding arm movable with respect to the fixed arm along the tool axis between a first position for receiving and releasing the implant and a second position for securely engaging the implant, the sliding arm comprising an internal surface for engaging the substantially planar portion of the second side surface of the implant such that as the sliding arm is advanced distally along the tool axis the increase in width of the implant between the first generally planar surface portion of the first side surface and the substantially planar surface of the second side surface increases as the substantially planar surface of the second side surface extends away from the first end surface results in a frictional engagement of the implant gripping mechanism with the implant.

8. The apparatus of claim 7, wherein the first end surface of the implant comprises a curved surface extending between the upper and lower bone engaging surfaces to define a rounded end portion.

9. The apparatus of claim 8, wherein the fixed arm of the implant gripping mechanism further comprises a first curved engagement surface for engaging the first end surface of the implant.

10. The apparatus of claim 9, wherein the sliding arm of the implant gripping mechanism further comprises a second curved engagement surface for engaging at least a portion of the rounded end portion of the first end surface of the implant.

11. The apparatus of claim 9, wherein the projection of the fixed arm comprises a tapered surface for engaging the transition surface of the implant.

* * * * *

UNITED STATES PATENT AND TRADEMARK OFFICE
CERTIFICATE OF CORRECTION

| | | |
|---|---|---|
| PATENT NO. | : 7,901,458 B2 | Page 1 of 1 |
| APPLICATION NO. | : 11/305604 | |
| DATED | : March 8, 2011 | |
| INVENTOR(S) | : Steven D. DeRidder et al. | |

It is certified that error appears in the above-identified patent and that said Letters Patent is hereby corrected as shown below:

Column 12, Line 44

Delete "substantiallyplanar" and insert --substantially planar--, therefor.

Signed and Sealed this

Eighth Day of November, 2011

David J. Kappos
*Director of the United States Patent and Trademark Office*